(12) United States Patent
Wang et al.

(10) Patent No.: US 9,808,209 B2
(45) Date of Patent: Nov. 7, 2017

(54) COLLIMATOR FOR USE IN A CT SYSTEM (71) Applicant: General Electric Company, Schenectady, NY (US)

(72) Inventors: Bin Wang, ChengDu (CN); Jiang Hsieh, Waukesha, WI (US); Xianjun Pan, Beijing (CN); Jiaqin Dong, Beijing (CN)

(73) Assignee: General Electric Company, Schenectady, NY (US)

( * ) Notice: Subject to any disclaimer, the term of this patent is extended or adjusted under 35 U.S.C. 154(b) by 203 days.

(21) Appl. No.: 14/135,808

(22) Filed: Dec. 20, 2013

(65) Prior Publication Data
US 2014/0185745 A1 Jul. 3, 2014

(30) Foreign Application Priority Data
Dec. 28, 2012 (CN) .............. 20120580454

(51) Int. Cl.
*A61B 6/03* (2006.01)
*A61B 6/06* (2006.01)
*G21K 1/02* (2006.01)
*A61B 6/00* (2006.01)

(52) U.S. Cl.
CPC ............ *A61B 6/032* (2013.01); *A61B 6/06* (2013.01); *A61B 6/4021* (2013.01); *A61B 6/4078* (2013.01); *A61B 6/582* (2013.01); *G21K 1/02* (2013.01)

(58) Field of Classification Search
CPC ........... A61B 6/032; A61B 6/582; A61B 6/06; A61B 6/4021; A61B 6/4078; G21K 1/02
See application file for complete search history.

(56) References Cited

U.S. PATENT DOCUMENTS

| 5,299,250 | A | | 3/1994 | Styrnol et al. |
| 5,469,429 | A | | 11/1995 | Yamazaki et al. |
| 5,644,614 | A | | 7/1997 | Toth et al. |
| 6,125,167 | A | * | 9/2000 | Morgan ................. H01J 35/10 378/121 |
| 6,385,278 | B1 | * | 5/2002 | Hsieh .................... A61B 6/032 378/15 |
| 7,317,786 | B2 | | 1/2008 | Distler et al. |
| 2006/0104415 | A1 | * | 5/2006 | Unger .................... A61B 6/06 378/62 |
| 2011/0007878 | A1 | * | 1/2011 | Dafni .................... G01T 1/2985 378/149 |

OTHER PUBLICATIONS

A dose reduction x-ray beam positioning system for high-speed multislice CT scanners, Med. Phys. vol. 27, No. 12, Dec. 2000.

* cited by examiner

*Primary Examiner* — Glen Kao (57) ABSTRACT

A collimator for use in a CT system made of an X-ray absorbing material, the collimator comprises an imaging aperture having a first width for passage of a first X-ray beam, the first X-ray beam being used for X-ray imaging, and a tracking aperture having a second width for passage of a second X-ray beam, the second X-ray beam being used for X-ray beam tracking.

17 Claims, 4 Drawing Sheets

COLLIMATOR FOR USE IN A CT SYSTEM

TECHNICAL FIELD

The present invention relates to medical scanning and, more particularly, to a collimator having a separate tracking aperture for a CT system and a corresponding method thereof.

BACKGROUND ART

With the development of medical technology, medical scanning is increasingly becoming an important diagnostic and therapeutic tool in many medical applications. For example, computed tomography (CT) has been widely used in the diagnosis and radiation treatment of patients. In CT systems, a fan-shaped beam projected by an X-ray source is calibrated (or collimated) to a X-Y plane, namely, "an imaging plane", of a Cartesian coordinate system. The X-ray beam penetrates the target object to be imaged (such as a patient) and arrives at a detector array after being attenuated by different parts of the target object. The attenuations of the X-ray beam are detected by the detector array so that an X-ray image (i.e., a CT image) can be formed.

Recently, increased attention and endeavor have been paid to reduce unnecessary radiation dose delivered to a patient. A commonly used method to reduce dose is to reduce the thickness of the X-ray beam in the longitudinal direction (namely, the Z-axis direction of the coordinate system of the CT system). Current CT manufacturers usually use a pre-patient collimator for extra X-ray beam obstruction. In the state of art, in order to accommodate the different requirements on the beam width in the Z-axis direction, two kinds of collimators have been designed. One kind of collimator has two aperture edges which can move independently to provide apertures of different widths. The other kind of collimator comprises one or more fixed width apertures.

The rotating gantry of the third generation CT systems introduces Z motion at different rotation angles. Since the X-ray tube is mounted rigidly on the gantry, the focal spot Z motion is introduced as the gantry rotates. The focal spot motion due to thermal expansion is another source of Z motion. On one hand, the collimator needs to have a narrow aperture for optimal dose reduction; on the other hand, a wide aperture is desired to accommodate the focal spot movement along the Z direction.

To overcome this contradiction, Toth et al proposed a method to dynamically track the motion of the focal spot of the X-ray source using Z ratio ("A dose reduction x-ray beam positioning system for high-speed multislice CT scanners", Med. Phys. Vol. 27, No. 12, December 2000). The contents of this article are incorporated by reference in its entirety into this application.

For other prior art technologies on focal spot tracking, reference can be made to U.S. Pat. No. 5,644,614, U.S. Pat. No. 7,317,786, U.S. Pat. No. 5,469,429, U.S. Pat. No. 5,299,250, and so on. The contents of these patents are also incorporated by reference in their entirety into this application.

Although these prior art technologies have alleviated the contradiction on the size of the collimator aperture to some extent, there are such problems as the existence of relatively large mutual interference between the aperture edges and failure to provide adequate tracking operation range in the use of prior art collimators with fixed aperture width. Especially for a fixed width sub-millimeter aperture, these problems are more serious.

In addition, existing collimators also have drawbacks in other aspects, such as poor tracking sensitivity and poor resistance to noise and other fluctuations. Therefore, there is a need for a solution to improve one or more aspects of the existing technology, thereby reducing mutual interference between the aperture edges in beam tracking, increasing tracking range, improving tracking sensitivity, enhancing anti-noise ability, or the like.

SUMMARY OF THE INVENTION

The present invention aims to solve one or more problems in the prior art. In particular, the present invention aims to achieve one or more of the following purposes in beam tracking: reducing mutual interference between the edges of the collimator aperture, increasing tracking range, improving tracking sensitivity, enhancing noise resistance, and so on.

According to one aspect of the present invention, a collimator for use in a CT system is provided. The collimator is made of an X-ray absorbing material and comprises: an imaging aperture having a first width for passage of a first X-ray beam, the first X-ray beam being used for X-ray imaging; and a tracking aperture having a second width for passage of a second X-ray beam, the second X-ray beam being used for X-ray beam tracking.

According to one embodiment of the present invention, the imaging aperture and the tracking aperture are aligned in a length direction.

According to one embodiment of the present invention, the second width is different from the first width.

According to one embodiment of the present invention, the second width is greater than the first width to reduce mutual interference caused by two edges of the tracking aperture.

According to one embodiment of the present invention, the second width is smaller than the first width to increase an operation range of beam tracking.

According to one embodiment of the present invention, the tracking aperture only includes a first tracking aperture.

According to one embodiment of the present invention, the tracking aperture includes a first tracking aperture and a second tracking aperture.

According to one embodiment of the present invention, the first tracking aperture and the second tracking aperture have an equal width.

According to one embodiment of the present invention, the width of the imaging aperture and the width of the tracking aperture are fixed.

According to one embodiment of the present invention, the tracking aperture has a rectangular shape and/or the imaging aperture has a rectangular shape.

According to one embodiment of the present invention, the tracking aperture and the imaging aperture are continuously formed.

According to one embodiment of the present invention, the tracking aperture has a width adapted to beam tracking using Z ratio, wherein Z-ratio refers to the ratio of the detector signal in the penumbra area to the detector signal in the umbra area of the tracking aperture.

According to one embodiment of the present invention, the width of the tracking aperture is adapted to determine a calibration curve and an operation range associated with Z-ratio.

According to a second aspect of the present invention, a CT system comprising a collimator according to one of the embodiments of the present invention is provided.

According to a third aspect of the present invention, a method for use in a CT system comprising a collimator made of an X-ray absorbing material is provided. The method comprises: allowing a first X-ray beam to pass through an imaging aperture for X-ray imaging, wherein the imaging aperture has a first width; and allowing a second X-ray beam to pass through a tracking aperture for X-ray tracking, wherein the tracking aperture has a second width.

The above improved solution of the present invention can solve one or more problems in the prior art. In particular, the present invention can achieve one or more of the following in beam tracking: reducing beam interference, increasing tracking range, improving tracking sensitivity, enhancing noise resistance, and so on.

BRIEF DESCRIPTION OF THE DRAWINGS

The advantages, features and characteristics of the present invention will be further understood through description of the specific embodiments of the present invention with reference to drawings, wherein.

DETAILED DESCRIPTION OF THE EMBODIMENTS

The present invention will be more completely described in the following with reference to the drawings, in which exemplary embodiments of the present invention are shown. However, it shall be understood that the present invention may be implemented in other different manners, and is not limited to these specific embodiments. Conversely, the provision of these embodiments is intended to make the disclosure of the present invention more thorough and complete so that the concept of the present invention can be completely understood by those skilled in the art. Throughout this application, identical or similar reference signs represent the same means or unit.

Figure 1:
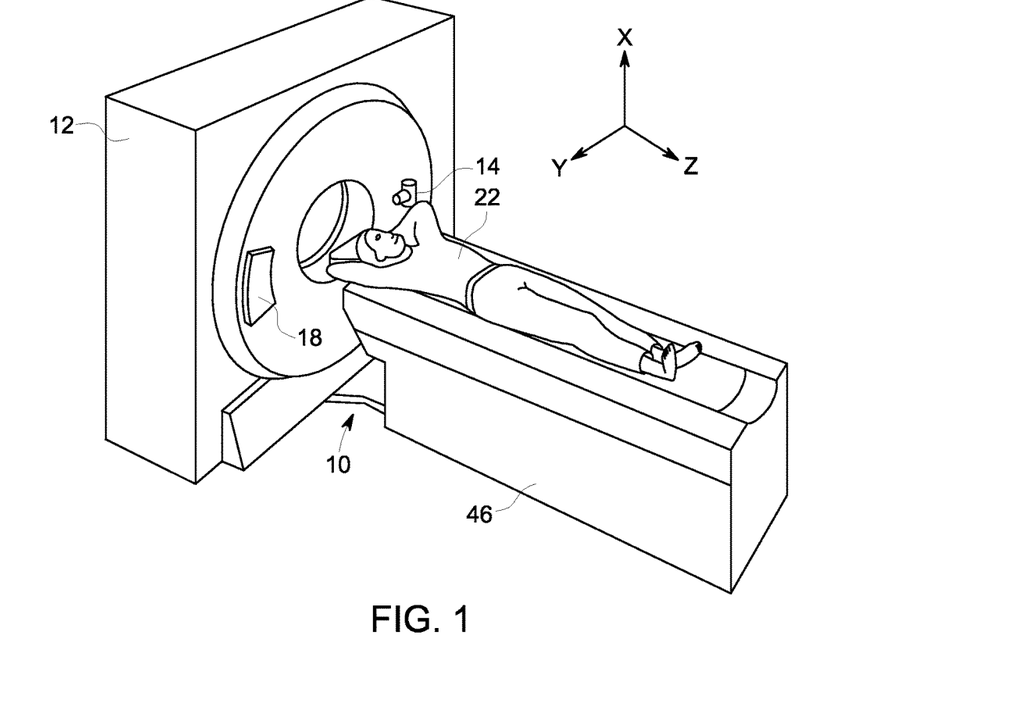
FIG. 1 shows a CT system according to one embodiment of the present invention.

FIG. 1 schematically shows a CT system 10 according to one embodiment of the present invention. The CT system 10 includes a gantry 12 in a third generation CT system. The gantry 12 includes an X-ray source 14 which projects fan-shaped X-ray beams onto a detector array 18 disposed on a side of the gantry 12 opposite to the X-ray source. The detector array 18 consists of a plurality of detector elements for joint detection of the X-rays penetrating a patient's body 22. Each detector element can generate an electrical signal indicating the intensity of the received X-rays and the attenuation of the X-rays after passing through the patient 22 on the table 46. Scans are performed to acquire X-ray projection data as the gantry 12 and the components mounted thereon revolve around the center of rotation of the gantry 12.

An X-ray source generally comprises a vacuum X-ray housing having an anode and a cathode. When a high voltage is applied across the anode and the cathode, X-rays are generated as electrons are accelerated from the cathode to focal spot (or focus) on the anode. In a CT system, an X-ray beam from the X-ray source is allowed to pass through a collimator for defining the contour or shape of the X-ray beam. The collimator made of an X-ray absorbing material has an aperture. The process of limiting or restricting an X-ray beam to a desired fan-shaped contour or shape by the collimator is referred to as "collimation".

Figure 2:
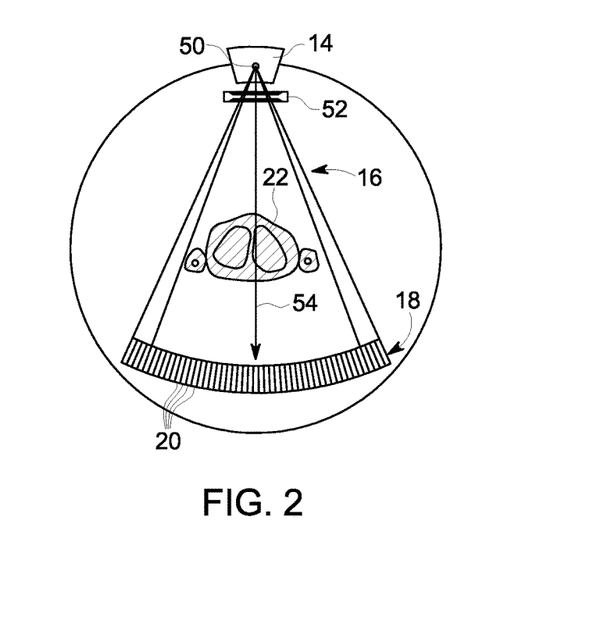
FIG. 2 shows an X-ray source according to one embodiment of the present invention.

FIG. 2 shows an X-ray source 14 according to one embodiment of the present invention. An X-ray beam 16 is emitted from a focal spot 50 of the X-ray source 14. After being collimated by a collimator 52, the X-ray beam 16 is projected to the detector array 18 formed by a plurality of detector elements 20 along a central axis 54 of the fan-shaped beam.

While the construction of a CT system of the present invention and an X-ray source thereof has been described above in connection with specific embodiments, it is not intended to limit the present invention thereto. Other implementations of the CT system and X-ray source are also applicable to the present invention.

Various ways can be used to track the X-ray beam. In X-ray beam tracking, it is necessary to use a control parameter to control the movement of the collimator aperture in the Z-axis direction (i.e., the longitudinal direction of the table) and to work out a calibration function mapping the control parameter to the beam position. The measured control parameter and the calibration function provide accurate beam position so that the direction and magnitude of the aperture movement along the Z-axis direction can be determined. The tracking control parameter and/or calibration function can be appropriately selected according to the design of the aperture (for example, the shape and movement characteristic of the aperture).

Figure 3:
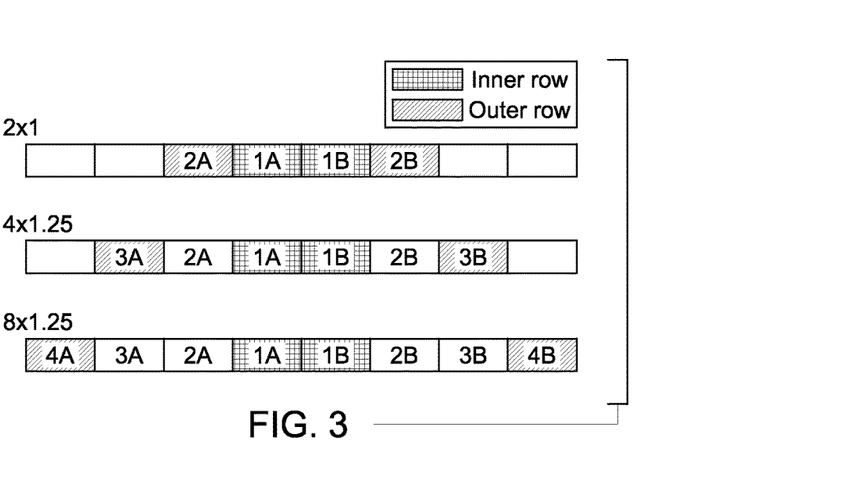
FIG. 3 shows inner rows and outer rows of tracking channels of a detector array according to one embodiment of the present invention.

According to one embodiment of the present invention, the ratio (namely, Z ratio) of the detector signal in the outer row (penumbra area) to the detector signal in the inner row (umbra area) of the detector array is used as the control parameter. FIG. 3 shows inner rows and outer rows of the tracking channels of a detector array according to some embodiments of the present invention. The parameters shown in FIG. 3 are commonly used in the art. For example, in the tracking channel at the top, the reference signs 1A and 1B indicate inner rows of the tracking channel of the detector array, and the reference signs 2A and 2B indicate the outer rows of the tracking channel. "2×1" indicates the number of detector rows covered by the collimator aperture multiplied by the equivalent size 1 mm of a single detector element in the Z-axis direction of the ISO center (i.e., the gantry center) plane.

In order to track beam using Z ratio, it is necessary to sweep the aperture in the Z-axis direction to obtain a calibration function or a Z-ratio curve (namely, a calibration curve) to map the Z ratio to the aperture position and, if necessary, to further map it to the beam position using geometry calculation. In the case where the two edges of the aperture can move independently relative to each other, in the sweep process for obtaining the Z-ratio curve, the first edge of the aperture is arranged to be away from the second edge, and then the second edge is swept to obtain a Z-ratio curve thereof. The Z-ratio curve of the first edge can be obtained in the same manner. Because the two edges can be arranged to be far away from each other, the influence of the mutual interference between the two edges can be effectively avoided in the Z ratio calculation. Meanwhile, a wider operation range for stable beam tracking can be obtained.

Figure 4:
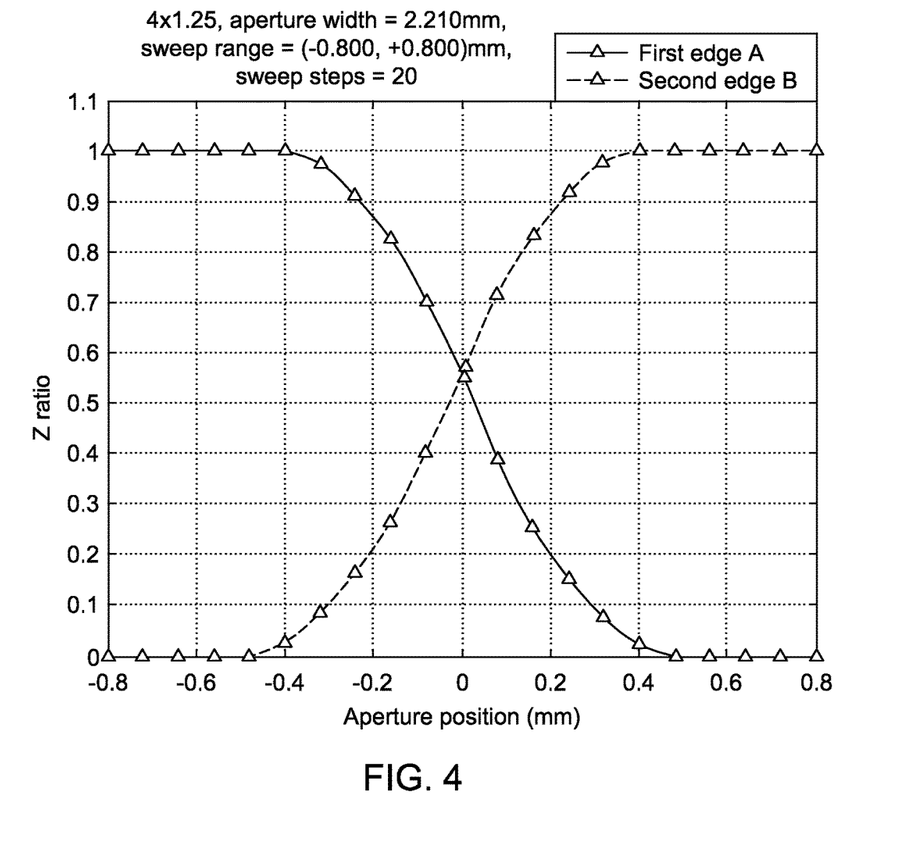
FIG. 4 shows Z-ratio curves of two aperture edges according to one embodiment of the present invention.

FIG. 4 shows the Z-ratio curves of two aperture edges according to one embodiment of the present invention. As shown, the horizontal axis represents the aperture position and the vertical axis represents the Z ratio; the solid line represents the Z-ratio curve of the first edge A, and the dotted line represents the Z-ratio curve of the second edge B. In this embodiment, the aperture width is 2.210 mm, the sweep range is (−0.800, +0.800) mm, and the sweep steps are 20.

According to some embodiments of the present invention, the aperture position refers to the Z-axis coordinate of the center line in the longitudinal direction of the aperture. In other embodiments, other positions may also be used to indicate the aperture position.

The manner to use Z-ratio for beam tracking, especially for obtaining Z ratio curves, determining the operation point and operation range, and so on, are well known in the art, and are not described in detail here.

For a collimator having a fixed width aperture, because the two edges of the aperture cannot move independently, there are problems in avoiding interference between the edges and providing enough beam tracking range. Such problems occur when the width of the collimator aperture is inappropriately selected (for example, overly wide or narrow).

Figure 5:
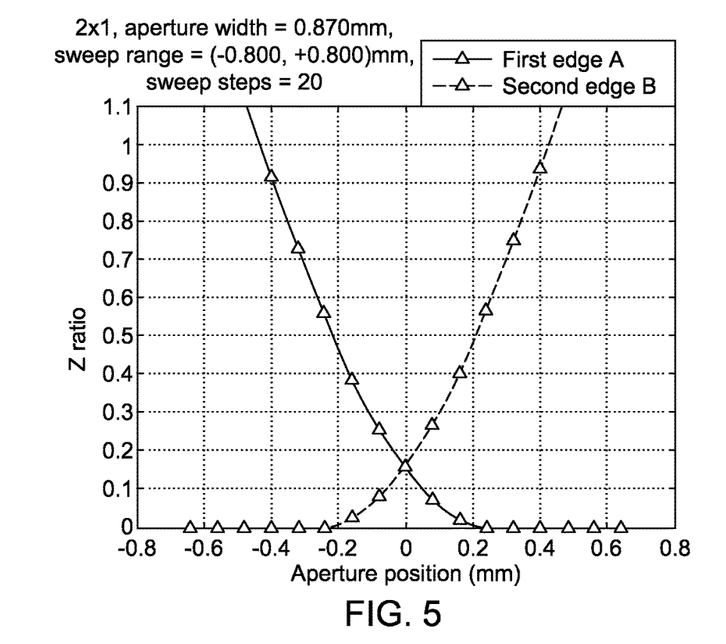
FIG. 5 shows Z-ratio curves for an aperture with a small fixed width.

For example, in the case that the narrowest beam width in the ISO center of the CT system is 0.625 mm to 1 mm and the nominal detector width in the Z-axis direction is 0.625 mm to 1.25 mm, if a fixed aperture width 0.6 mm to 1 mm (nominal width at ISO) is used, then there will be great mutual interference between the edges, and the Z ratio obtained will not be the ratio of the signal in the penumbra area to the signal in the umbra area. In this situation, the inner row contains some penumbra signal, so the Z ratio of the operation point only has a very small value (e.g., less than 0.2). Thus, using a narrow fixed-width aperture will result in poor resistance to noise and other fluctuation and failure to provide a stable beam tracking operation point and operation range. FIG. 5 shows the Z-ratio curves for an aperture with a small fixed width.

Figure 6:
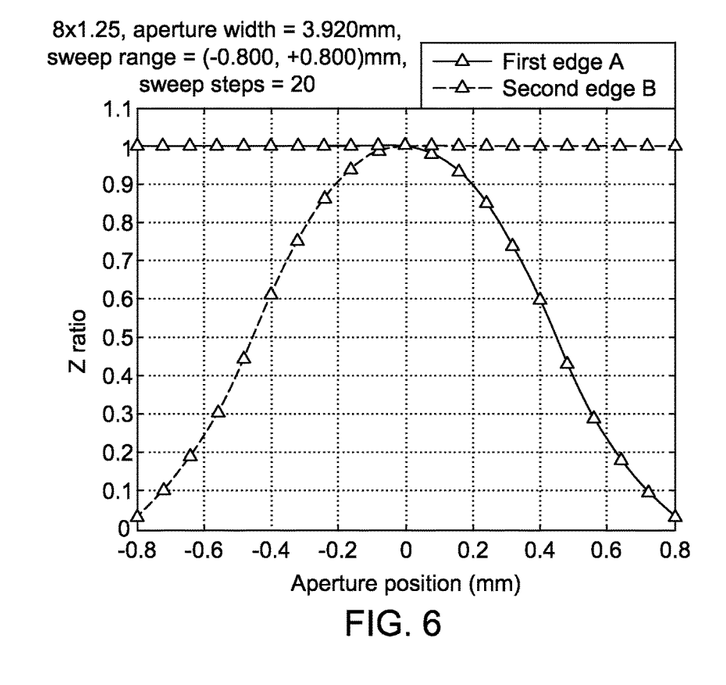
FIG. 6 shows Z-ratio curves for an aperture with a large fixed width.

As another example, for a collimator aperture having a larger width such as one for use in a 8×1.25 mm detector, the aperture width at the corresponding imaging channels should be wide enough to cover the 8×1.25 mm detector. However, with an aperture of such width, the Z ratio of the outer row and the inner row of the tracking channel will be very close to 1 in a large range and thus cannot provide sufficient operation range in the calibration curve. FIG. 6 shows the Z-ratio curves for an aperture with a large fixed width.

Figure 7:
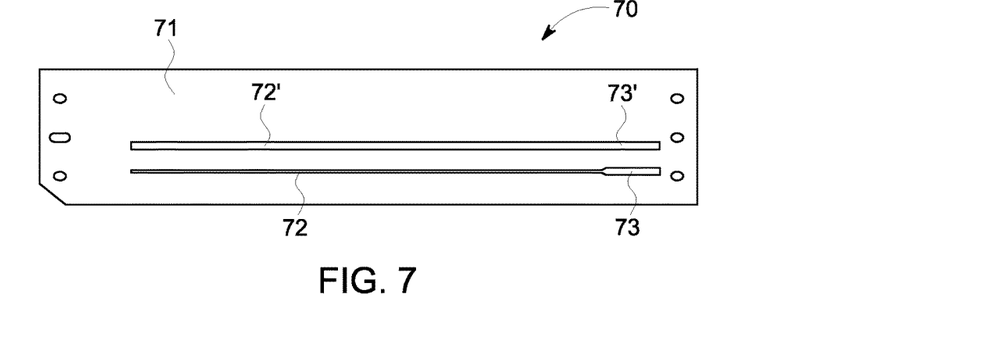
FIG. 7 shows a collimator for use in a CT system according to one embodiment of the present invention.

FIG. 7 shows a collimator 70 for use in a CT system according to one embodiment of the present invention. The collimator 70 is made of an X-ray absorbing material 71 and comprises imaging apertures 72, 72' and tracking apertures 73, 73'. X-rays emitted from the X-ray source and passing through the imaging aperture form a first X-ray beam for X-ray imaging, and X-rays emitted by the X-ray source and passing through the tracking aperture form a second X-ray beam for X-ray beam tracking. The use of X-ray beams for X-ray imaging and beam tracking is well known in the art and are not described in detail here.

As shown in FIG. 7, the width of the imaging apertures 72, 72' may be different from the width of the tracking apertures 73, 73', and the imaging apertures and the tracking apertures are aligned in the longitudinal direction, i.e., the center line of the imaging aperture extending in the length direction thereof and the center line of the tracking aperture extending in the length direction thereof are in the same straight line or substantially in the same straight line.

According to one embodiment of the present invention, the center line of the imaging aperture extending in the length direction thereof and the center line of the tracking aperture extending in the length direction thereof are slightly misaligned. For example, for a 8×1.25 mm detector array, if the imaging aperture corresponds to rows 1-8 of the detectors in the imaging channel of the detector array, then the tracking aperture corresponding to the width of 4 rows of detectors can be selected as corresponding to rows 1-4, 2-5, 3-6, 4-7 or 5-8 of the imaging channel. In fact, as long as the size of the slight misalignment is such that the X-rays passing through the tracking aperture still can be detected by the detectors of the tracking channel, then such a slight misalignment is allowed.

It will be appreciated that the collimator as shown in FIG. 7 is exemplary only and is not intended to limit the present invention thereto. For example, while the collimator as shown in FIG. 7 comprises two pairs of apertures 72, 72' and 73, 73', a skilled person in the art would understand that the collimator may comprise only one pair of apertures (i.e., an imaging aperture and a tracking aperture); or, alternatively, the collimator may include more than two pairs of apertures. In addition, although the imaging aperture and the tracking aperture that are aligned with each other have different widths as shown in FIG. 7, they can have the same width in some particular applications.

According to one embodiment of the present invention, the width of the tracking aperture is larger than the width of the imaging aperture. Because the collimator is provided with an imaging aperture and a tracking aperture respectively, and because the two apertures can independently have different widths, the requirement on the width of the imaging aperture imposed by the beam width required for CT imaging has no influence on the width of the tracking aperture for beam tracking. For example, for a narrow beam width such as 2×0.625 mm or 2×1 mm for a 1.25 mm detector width, the imaging aperture width at the imaging channels can be designed to make the umbra area associated with the imaging aperture to cover two rows of detectors, and the tracking aperture width at the beam tracking channels can be designed to make the umbra area associated with the tracking aperture to cover more than four rows of detectors. Thus, by selecting appropriate width for the imaging aperture and appropriate width for the tracking aperture, it is possible to reduce the beam interference caused by the two edges of the tracking aperture while ensuring the beam width required for imaging.

According to one embodiment of the present invention, the width of tracking aperture is smaller than the width of the imaging aperture. For example, for a wider beam width such as 8×0.625 mm for an 8×1.25 mm detector width, the imaging aperture width at the imaging channels should be such that all the 8 rows of detectors are in the umbra area. If the same aperture width is used at the beam tracking channels, then the Z ratio will be very close to 1 in a large range of the aperture z position since both the inner row and the outer row fall within the umbra area. As a result, the Z ratio is insensitive to the movement of the focal spot of the X-ray source. For this situation, a tracking aperture width narrower than the imaging aperture width, for example, one that covers 4 rows, 6 rows, a part of the 8 rows of the detectors, may be selected. Therefore, since the requirement on the width of the imaging aperture imposed by the beam width required for CT imaging has no influence on the width of the tracking aperture, the selection of appropriate widths for the imaging aperture and the tracking aperture can provide larger beam tracking operation range while ensuring the beam width required for imaging.

According to one embodiment of the present invention, the collimator comprises just one tracking aperture. The tracking aperture can be located at any position that is aligned with the imaging aperture in the length direction, for example, a position to the left or to the right of the imaging aperture. Alternatively, the tracking aperture may not be aligned with the imaging aperture in the length direction, but is slightly misaligned with the latter.

According to one embodiment of the present invention, the tracking aperture may also comprise two apertures, such as a first tracking aperture and a second tracking aperture. The first tracking aperture and the second tracking aperture may be disposed at any position that is aligned or slightly misaligned with the imaging aperture in the length direction, and may have the same or different widths. For example, the first tracking aperture and the second tracking aperture having the same or different widths may be located at the two sides of the imaging aperture respectively.

According to one embodiment of the present invention, the imaging aperture and the tracking aperture may have fixed width. For a tracking aperture having fixed width, the operation point may correspond to the position of the Z ratio curve where the aperture position=0, or other suitable positions. It will be understood that it is also possible to design at least one of the imaging aperture and the tracking aperture as having a variable width. For example, the two edges of the imaging aperture are designed as independently movable, and the tracking aperture is designed as having fixed width. Such a design can reduce the number of times in adjusting the aperture width when using fan-shaped beams of different widths for X-ray imaging.

According to one embodiment of the present invention, both the tracking aperture and the imaging aperture have an elongated, rectangular shape, as shown in FIG. 7. However, depending on needs of the specific applications, the tracking aperture and the imaging aperture can also adopt other suitable shapes, such as an elongated rhombus.

According to one embodiment of the present invention, the tracking aperture and the imaging aperture are continuously formed and there is no X-ray absorbing material therebetween. However, it will be appreciated that, depending on the actual applications, the tracking aperture and the imaging aperture can also be discretely formed and separated by X-ray absorbing material to block more X-rays.

In the above the embodiments of the present invention have been described in connection with beam tracking using Z ratio, wherein the tracking aperture has a width adapted to determine a calibration curve and an operation range associated with the Z ratio. However, persons skilled in the art will appreciate that a collimator having separate tracking aperture and imaging aperture can also be used in other tracking solutions.

In one embodiment of the present invention, the asymmetry degree $R=(A-B)/(A+B)$ of the X ray signals at side A and side B may be used for beam tracking, wherein A represents the detector row signal at side A of the tracking channel, and B represents detector row signal at side B of the tracking channel. For example, for a tracking channel having 8 rows of detectors, A can represent the signals of the 4 rows of detectors on the left side, and B can represent the signals of the 4 rows of detectors on the right side. In the tracking mode using the asymmetry degree R, in the case of a wide aperture (e.g., 8×1.25 mm), if the tracking aperture and the imaging aperture use the same width, then the asymmetry degree R will be very flat at the operation point, i.e., insensitive to the focal spot movement. In this case, correspondingly narrowing the tracking aperture can improve the tracking sensitivity.

Figure 8:
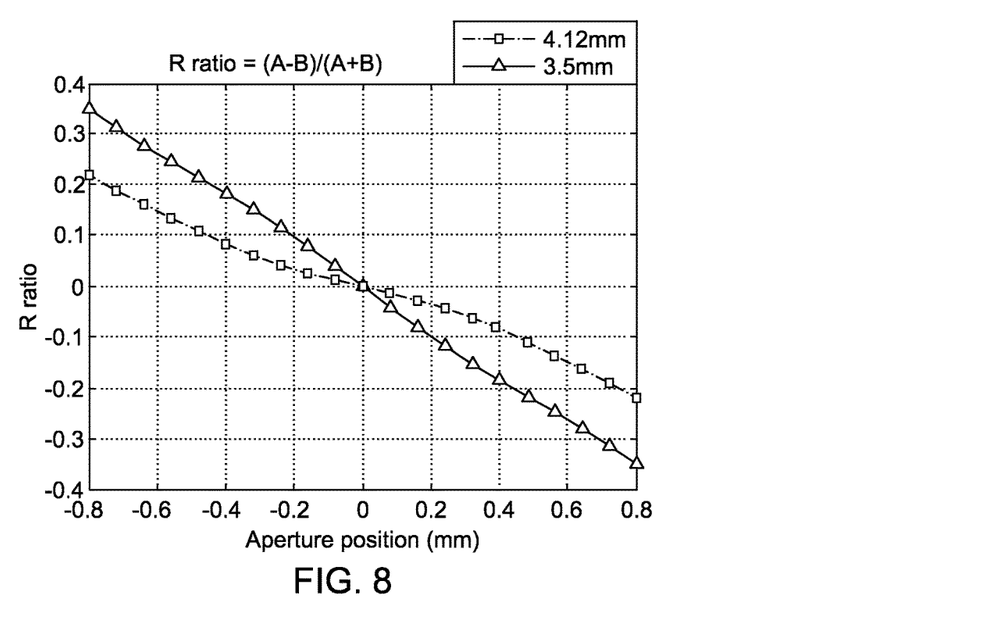
FIG. 8 shows R ratio curves corresponding to different aperture widths.

FIG. 8 shows the R ratio curves corresponding to different aperture widths, wherein the horizontal axis represents the aperture position, and the vertical axis represents the R value. In FIG. 8, the dotted line indicates the change of the R ratio when the aperture width is 4.12 mm, and the solid line indicates the change of the R ratio when the aperture width is 3.5 mm.

According to one embodiment of the present invention, there is also provided a CT system comprising a collimator as described above. The collimator as used in the CT system is made of an X-ray absorbing material and comprises separate imaging aperture and tracking aperture. The width of the imaging aperture allows passage of X-rays for X-ray imaging and the width of the tracking aperture allows passage of X-rays for X-ray tracking. It will be appreciated that the collimator used in the CT system can also comprise one or more features as described above.

The collimator according to the present invention can be used in existing CT systems and possible future CT systems for tracking X-ray beams. By using the collimator according to the present invention, mutual interference between the edges can be reduced and meanwhile a relatively large tracking operation range can be provided in X-ray beam tracking.

Figure 9:
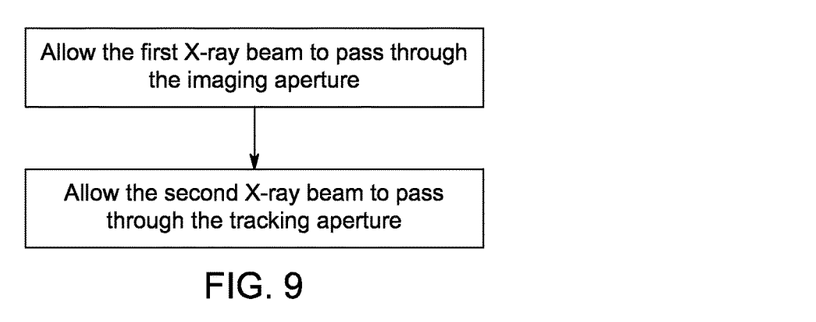
FIG. 9 illustrates a method for use in a CT system according to one embodiment of the present invention.

FIG. 9 illustrates a method for use in a CT system according to one embodiment of the present invention, wherein the CT system comprises a collimator made of an X-ray absorbing material. In the method, a first X-ray beam is allowed to pass through an imaging aperture for X-ray imaging and a second X-ray beam is allowed to pass through a tracking aperture for X-ray tracking. The imaging aperture has a first width and the tracking aperture has a second width.

According to one embodiment of the present invention, the imaging aperture and the tracking aperture are aligned in the length direction.

According to one embodiment of the present invention, the second width of the tracking aperture is different from the first width of the imaging aperture.

According to one embodiment of the present invention, the second width is arranged to be greater than the first width to reduce the mutual interference caused by two edges of the tracking aperture.

According to one embodiment of the present invention, the second width is arranged to be smaller than the first width to provide an improved operation range of beam tracking.

According to one embodiment of the present invention, the tracking aperture includes a first tracking aperture.

According to one embodiment of the present invention, the tracking aperture includes a first tracking aperture and a second tracking aperture.

According to one embodiment of the present invention, the first tracking aperture and the second tracking aperture are arranged to have the same width.

According to one embodiment of the present invention, the first width of the imaging aperture and the second width of the tracking aperture are fixed.

According to one embodiment of the present invention, the tracking aperture has a rectangular shape and/or the imaging aperture has a rectangular shape.

According to one embodiment of the present invention, the tracking aperture and the imaging aperture are continuously formed.

According to one embodiment of the present invention, the tracking aperture is used for Z ratio beam tracking. As stated above, Z-ratio refers to the ratio of the detector signal in the penumbra area to the detector signal in the umbra area of the tracking aperture.

According to one embodiment of the present invention, the tracking aperture is used to determine a calibration curve and an operation range associated with Z-ratio.

According to one embodiment of the present invention, the current Z ratios of the two edges of the tracking aperture are determined during X-ray beam tracking.

According to one embodiment of the present invention, if the current Z ratios of the two edges both fall within the operation range of the calibration curve, then the current Z ratios of the two edges are used to move the tracking aperture to minimize the average distance between the two edges of the tracking aperture and the operation point.

According to one embodiment of the present invention, if only the current Z ratio of one edge falls within the operation range of the calibration curve, then the Z ratio of the one edge is used to move the tracking aperture to minimize the average distance between the two edges of the tracking aperture and the operation point.

According to one embodiment of the present invention, if neither of the current Z ratios of the two edges fall within the operation range of the calibration curve, then the tracking aperture is moved a first distance in a first direction of the Z-axis of the CT system; then the current Z ratios of the two edges of the tracking aperture are calculated; and the calculated current Z-ratios are used to perform X-ray beam tracking, wherein:

if the current Z ratios of the two edges both fall within the operation range of the calibration curve, then the Z ratios of the two edges are used to move the tracking aperture to minimize the average distance between the two edges of the tracking aperture and the operation point; or if only the current Z ratio of one edge falls within the operation range of the calibration curve, then the Z ratio of the one edge is used to move the tracking aperture to minimize the average distance between the two edges of the tracking aperture and the operation point.

According to one embodiment of the present invention, if, after the tracking aperture has been moved a first distance, neither of the current Z ratios of the two edges of the tracking aperture fall within the operation range of the calibration curve, then the tracking aperture is moved a second distance in a second direction of the Z-axis of the CT system, wherein the second direction is opposite to the first direction and the second distance is greater than the first distance; after movement of the second distance, the current Z ratios of the two edges of the tracking aperture are calculated; and the calculated current Z-ratios are used to perform X-ray beam tracking, wherein:

if the current Z ratios of the two edges both fall within the operation range of the calibration curve, then the Z ratios of the two edges are used to move the tracking aperture to minimize the average distance between the two edges of the tracking aperture and the operation point; or if only the current Z ratio of one edge falls within the operation range of the calibration curve, then the Z ratio of the one edge is used to move the tracking aperture to minimize the average distance between the two edges of the tracking aperture and the operation point; or if neither of the current Z ratios of the two edges of the tracking aperture fall within the operation range of the calibration curve, then aborting X-ray tracking and/or reporting an error.

It will be understood by those skilled in the art that the present invention can be realized in various known ways in this field, including, but not limited to: hardware, firmware, computer program, logical means, etc.

Through the above description and the corresponding drawings, the preferred embodiments of the present invention have been revealed in detail. Besides, though some special terms are used in the text, they are intended to be exemplary only. Those skilled in the art will appreciate that various modifications, equivalent replacements, changes, and so on may be made to the present invention. For example, one step or module in the above embodiments may be divided into two or more steps or modules for implementation, or conversely, two or more steps or functions of modules or means in the above embodiments are put into one step or module for implementation. As long as these changes do not depart from the spirit of the present invention, they should come within the protection scope claimed in the present application. The protection scope of the present invention is defined by the attached claims.

The present invention can improve one or more aspects of the prior art and thus can achieve one or more of the following in beam tracking: reducing beam interference, increasing tracking range, improving tracking sensitivity, enhancing noise resistance, and so on.

Although specific features of various embodiments of the present disclosure may be shown in and/or described with respect to some drawings and not in others, this is for convenience only. It is to be understood that the described features, structures, and/or characteristics may be combined and/or used interchangeably in any suitable manner in the various embodiments, for example, to construct additional assemblies and techniques.

What is claimed is:

1. A CT system, comprising:
a collimator made of an X-ray absorbing material and a processor, wherein the collimator comprises:
an imaging aperture having a first substantially constant width for passage of a first X-ray beam, the first X-ray beam being used for X-ray imaging; and
a tracking aperture having a second substantially constant width for passage of a second X-ray beam, the second X-ray beam being used for X-ray beam tracking, the tracking aperture being an extension of the imaging aperture; and
wherein the processor is configured to configure a width of the tracking aperture to determine a calibration curve associated with a Z-ratio, said Z-ratio representing a ratio of a detector signal in a penumbra area to a detector signal in an umbra area of the tracking aperture.

2. The CT system according to claim 1, wherein the imaging aperture and the tracking aperture are aligned in a length direction.

3. The CT system according to claim 2, wherein the second width is different from the first width.

4. The CT system according to claim 3, wherein:
the second width is greater than the first width to reduce mutual interference caused by two edges of the tracking aperture, or
the second width is smaller than the first width to increase an operation range of the X-ray beam tracking.

5. The CT system according to claim 4, wherein the tracking aperture only includes a first tracking aperture.

6. The CT system according to claim 4, wherein the tracking aperture includes a first tracking aperture and a second tracking aperture.

7. The CT system according to claim 6, wherein the first tracking aperture and the second tracking aperture have an equal width.

8. The CT system according to claim 1, wherein the width of the imaging aperture and the width of the tracking aperture are fixed.

9. The CT system according to claim 1, wherein the tracking aperture has a rectangular shape and/or the imaging aperture has a rectangular shape.

10. The CT system according to claim 1, wherein the tracking aperture and the imaging aperture are continuously formed.

11. A method for use in a CT system comprising a collimator made of an X-ray absorbing material, the method comprising:
allowing a first X-ray beam to pass through an imaging aperture for X-ray imaging, wherein the imaging aperture has a first substantially constant width; and
allowing a second X-ray beam to pass through a tracking aperture for X-ray tracking, wherein the tracking aperture has a second substantially constant width, the tracking aperture being an extension of the imaging aperture; and
configuring, by a system using a processor, a width of the tracking aperture to determine a calibration curve associated with a Z-ratio, said Z-ratio representing a ratio of a detector signal in a penumbra area to a detector signal in an umbra area of the tracking aperture.

12. The method according to claim 11, wherein the imaging aperture and the tracking aperture are aligned in a length direction.

13. The method according to claim 12, wherein the second width is different from the first width.

14. The method according to claim 11, wherein the first width of the imaging aperture and the second width of the tracking aperture are fixed.

15. The method according to claim 11, wherein the tracking aperture is arranged to have a rectangular shape and/or the imaging aperture is arranged to have a rectangular shape.

16. The method according to claim 11, wherein the tracking aperture is continuously formed with the imaging aperture.

17. The method according to claim 11, wherein the tracking aperture is used to perform Z-ratio beam tracking.

\* \* \* \* \*